United States Patent [19]
Hiramoto et al.

[11] Patent Number: 6,008,499
[45] Date of Patent: Dec. 28, 1999

[54] SYNCHROTRON TYPE ACCELERATOR AND MEDICAL TREATMENT SYSTEM EMPLOYING THE SAME

[75] Inventors: Kazuo Hiramoto, Hitachiota; Masumi Umezawa; Koji Matsuda, both of Hitachi, all of Japan

[73] Assignee: Hitachi, Ltd., Tokyo, Japan

[21] Appl. No.: 08/984,520

[22] Filed: Dec. 3, 1997

[30] Foreign Application Priority Data

Dec. 3, 1996 [JP] Japan .................................... 8-322483

[51] Int. Cl.⁶ .................................................. H05H 13/04
[52] U.S. Cl. ........................ 250/492.3; 315/503; 315/507
[58] Field of Search ........................ 250/492.3; 315/503, 315/507

[56] References Cited

U.S. PATENT DOCUMENTS

| 4,870,287 | 9/1989 | Cole et al. ............................. 250/492.3 |
| 5,363,008 | 11/1994 | Hiramoto et al. ........................ 313/62 |
| 5,698,954 | 12/1997 | Hirota et al. ............................ 315/503 |

OTHER PUBLICATIONS

"Proceedings of the 1995 Particle Accelerator Conference", May 1–5, 1995, "Lattice Design of Indiana University Cyclotron Facility Cooler Injector Synchrotron", D. Li et al, Indiana University Cyclotron Facility, Bloomington, IN.

The 8th Symp. on Accelerator Science and Technology, 1991, Saitama, Japan, pp. 413–415.

Primary Examiner—Edward P. Westin
Assistant Examiner—Nikita Wells
Attorney, Agent, or Firm—Antonelli, Terry, Stout & Kraus, LLP

[57] ABSTRACT

An object of the present invention is to provide a small synchrotron type accelerator and a medical treatment system employing the same. In order to attain this object, according to the present invention, a synchrotron type accelerator includes: a deflecting electromagnet which is arranged on a circulating orbit of a charged particle beam; a first deflector for beam ejection by which the charged particle beam turning along the circulating orbit is deflected; and a second deflector for beam ejection which is used in pairs with the first deflector for beam ejection and by which the charged particle beam which has been deflected by the first deflector for beam ejection is introduced into an ejected beam transporting system, wherein both the deflecting electromagnet and the second deflector for beam ejection are arranged in this order downstream with respect to the first deflector for beam ejection.

7 Claims, 6 Drawing Sheets

SYNCHROTRON TYPE ACCELERATOR AND MEDICAL TREATMENT SYSTEM EMPLOYING THE SAME

BACKGROUND OF THE INVENTION

The present invention relates to a synchrotron type accelerator and a medical treatment system employing the same.

A conventional synchrotron dedicated to medical use is described in an article of Proc. of the 8-th Symposium on Accelerator Science and Technology, 1991, Saitama, Japan, p.414 (FIG. 3).

A conventional synchrotron type acceleration is shown in FIG. 5. When ejecting a charged particle beam, a multipolar electromagnet 11 for resonance excitation is excited so that the resonance of the betatron oscillations of the charged particle beam causes the amplitude of the betatron oscillations to increase. Then, the charged particle beam having the increased amplitude of the betatron oscillations is ejected to a medical treatment room 1010 through an electrostatic deflector 101 and a deflecting electromagnet 102 which are arranged in a straight section for use in ejecting therethrough the charged particle beam.

The electrostatic deflector 101 is shown in FIG. 6. A high voltage is applied across electrodes 1031 and 1032 by a power source 131 to generate a horizontal electric field. The charged particle beam which enters into a space defined between the electrodes 1031 and 1032 due to increase of the amplitude of the betatron oscillations is deflected by the horizontal electric field to enter into an ejected beam transporting system to be ejected therethrough. On the other hand, the charged particles which did not enter into the space between the electrodes 1031 and 1032 circulate along the accelerator without being ejected. Then, the amplitude of the betatron oscillations of such charged particles are again increased and then are ejected through the ejected beam transporting system just after having entered into the space between the electrodes.

The deflecting electromagnet 102 for the beam ejection is shown in FIG. 7. At the time when a current is supplied from a power source 131 to coils 1041 and 1042, the vertical magnetic field is generated between the coils 1041 and 1042. The charged particle beam is further deflected by this vertical magnetic field to be ejected to the ejected beam transporting system.

In the electrostatic deflector 101, the charged particle beam which has collided with the end face of the electrode 1031 is lost. Therefore, in order to minimize the beam loss, the electrode 1031 needs to be thin. In the case of the deflector of the electrostatic type, however, it is difficult to increase the electric field strength up to a level equal to or larger than 90 kV/cm, and hence it is impossible to deflect sufficiently the charged particle beam.

In the deflecting electromagnet 102 for beam ejection, in order to suppress the heating of the coils, the coil 1041 is thickened. However, since the charged particle beam collides with the coil 1041, this results in the beam loss being increased.

In the conventional synchrotron, as shown in FIG. 5, in which the electrostatic deflector 101 is provided upstream, and the deflecting electromagnet 102 for beam ejection is provided downstream, both the electrostatic deflector 101 and the deflecting electromagnet 102 for beam ejection have to be long enough in the charged particle beam travelling direction in order to deflect sufficiently the charged particle beam in the electrostatic deflector 101 and also to reduce the beam loss in the deflecting electromagnet 102 for beam ejection. As a result, the dimensions of the synchrotron becomes large.

SUMMARY OF THE INVENTION

An object of the present invention is to provide a small synchrotron type accelerator.

In order to attain the above-mentioned object, the first feature of the present invention is provided by a synchrotron type accelerator including: a deflecting electromagnet which is arranged on a circulating orbit of a charged particle beam; a first deflector for beam ejection by which the charged particle beam circulating along the circulating orbit is deflected; and a second deflector for beam ejection which is used in pairs with the first deflector for beam ejection and by which the charged particle beam which has been deflected by the first deflector for beam ejection is introduced into an ejected beam transporting system, wherein the deflecting electromagnet and the second deflector for beam ejection are arranged in this order downstream with respect to the first deflector for beam ejection. Since the deflecting electromagnet and the second deflector for beam ejection are arranged in the order of the deflecting electromagnet and the second deflector for beam ejection downstream with respect to the first deflector for beam ejection, i.e., the first deflector for beam ejection and the second deflector for beam ejection are not arranged between the deflecting electromagnet and another deflecting electromagnet adjacent thereto, it is possible to shorten the distance between the deflecting electromagnet and another deflecting electromagnet adjacent thereto. Therefore, the synchrotron type accelerator can be miniaturized.

The second feature of the present invention is that four-poles divergence electromagnets are arranged in the positions which are downstream with respect to the first deflector for beam ejection and also are upstream with respect to the second deflector for beam ejection. By arranging the four-poles divergence electromagnets in the positions downstream with respect to the first deflector for beam ejection and also upstream with respect to the second deflector for beam ejection, the charged particle beam which has been deflected by the first deflector for beam ejection can be further deflected in the direction of deflecting the charged particle beam through the first deflector for beam ejection. Therefore, the structure of the first deflector for beam ejection and the second deflector for beam ejection can be shortened in the charged particle beam circulating direction, and hence the synchrotron type accelerator can be miniaturized. In addition, the charged particle beam which has been sufficiently deflected by the four-poles divergence electromagnets is introduced into the ejected beam transporting system without colliding with the second deflector for beam ejection. In such a way, since it is possible to prevent the charged particle beam from colliding with the second deflector for beam ejection, the beam loss is reduced and hence the ejection efficiency can be enhanced.

The third feature of the present invention is that the deflecting electromagnet makes the charged particle beam diverge in the direction of deflecting the charged particle beam through the first deflector for beam ejection, whereby the charged particle beam is sufficiently deflected, and hence the structure of the first deflector for beam ejection and the second deflector for beam ejection can be shortened in the charged particle beam travelling direction. As a result, the synchrotron type accelerator can be miniaturized. In addition, since the number of four-poles divergence electromagnets each of which serves to make the charged particle beam diverge, the synchrotron type accelerator can be further miniaturized.

The fourth feature of the present invention is provided by providing power sources for supplying electric power, which is used to generate an electric field or a magnetic field, to the first deflector for beam ejection, the second deflector for beam ejection, the four-poles divergence electromagnets and the deflecting electromagnet, respectively, and control means for controlling the electric power in such a way that the stability limit of the resonance of the betatron oscillations of the charged particle beam, and the magnitude of the electric field or the magnetic field are maintained substantially fixed. The stability limit of the resonance of the betatron oscillations of the charged particle beam, and the magnitude of the electric field or the magnetic field are maintained substantially fixed, whereby since the orbit of the charged particle beam which enters into the second deflector for beam ejection while the charged particle beam is being ejected is not substantially changed, it is possible to obtain the ejected beam having the substantially fixed ejection angle. Therefore, the collision of the ejected beam with the second deflector for beam ejection or the beam duct can be prevented, and hence the beam loss can be reduced and the ejection efficiency increased.

The fifth feature of the present invention is provided by providing a synchrotron type accelerator having the above-mentioned fourth feature, an ejected beam transporting system for transporting the charged particle beam which has been ejected from the synchrotron type accelerator, and an irradiation system connected to the ejected beam transporting system for applying the charged particle beam which has been transported by the ejected beam transporting system to a patient. According to this feature, since the ejected beam can be obtained from the synchrotron type accelerator with high ejection efficiency, the irradiation quantity required for applying the charged particle beam to a patient can be obtained for a short irradiation time period.

BRIEF DESCRIPTION OF THE DRAWINGS

The above and other objects as well as advantages of the present invention will become clear by the following description of the preferred embodiments of the present invention with reference to the accompanying drawings, wherein.

DESCRIPTION OF THE PREFERRED EMBODIMENTS

Figure 1:
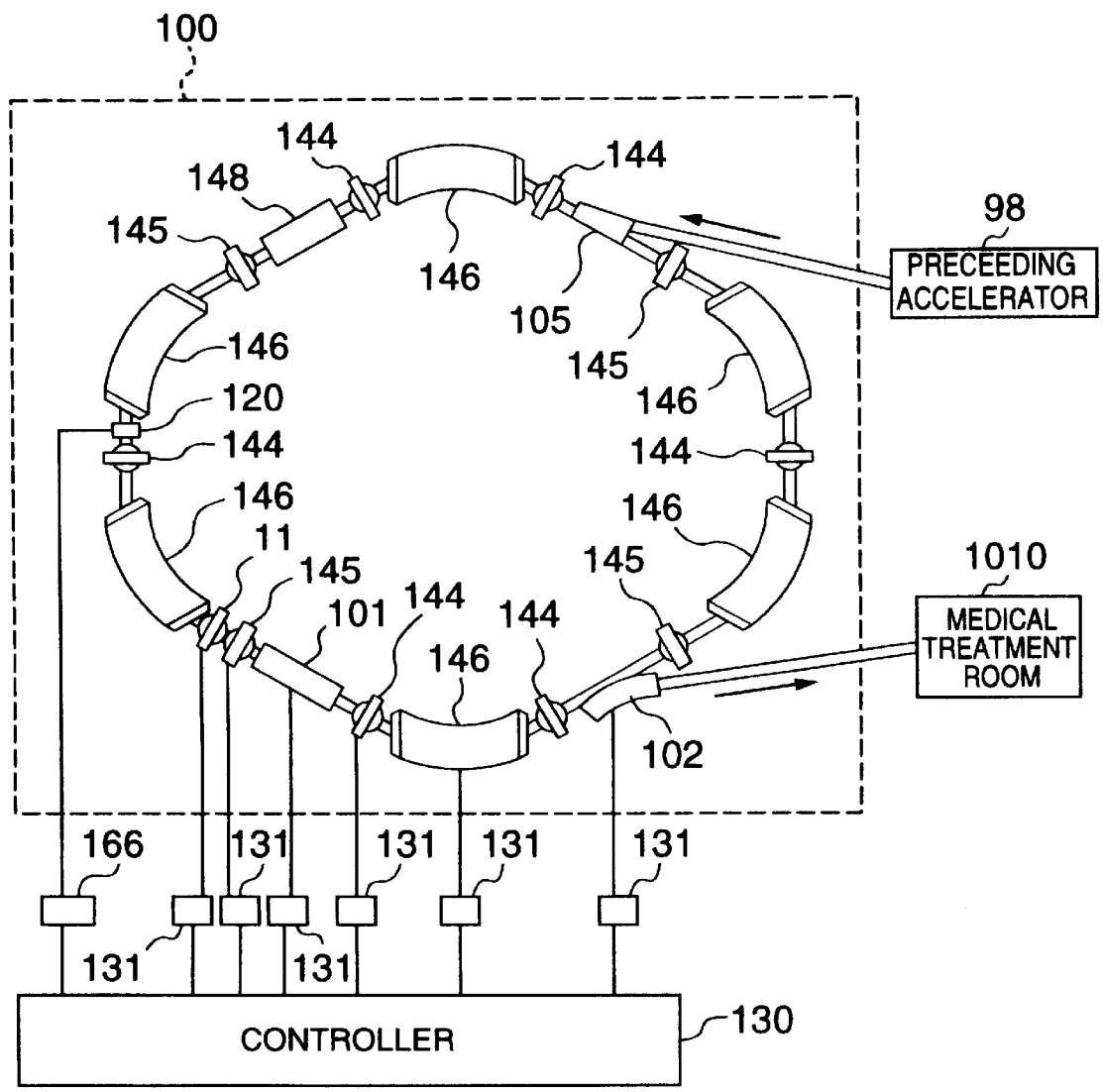
FIG. 1 is a schematic view, partly in block diagram, showing a of a synchrotron type accelerator as a preferred embodiment of the present invention.

The preferred embodiments of the present invention will hereinafter be described in detail with reference to the accompanying drawings.

Firstly, a synchrotron type accelerator 100 as a first embodiment of the present invention will hereinbelow be described with reference to FIG. 1.

In the accelerator 100 of the present embodiment, a charged particle beam having low energy is injected from a preceeding accelerator 98 to the accelerator 100 and after acceleration, is ejected into a medical treatment room 1010 by utilizing the resonance of the betatron oscillations of the charged particle beam.

The accelerator 100 includes four-poles convergence electromagnets 145, four-poles divergence electromagnets 144 and a multipolar electromagnet 11 for resonance excitation by which the stability limit of the resonance is determined, an electrostatic deflector 101 for beam ejection and a deflecting electromagnet 102 for beam ejection, and a high frequency applying unit 120 for beam ejection through which the betatron oscillations are increased to exceed the stability limit of the resonance. Two four-poles divergence electromagnet 144 and a deflecting electromagnets 146 are arranged between the electrostatic deflector 101 and the deflecting electromagnet 102 for beam ejection. In addition, the deflecting electromagnet 146 is arranged between the two four-poles divergence electromagnets 144. The four-poles convergence electromagnet 145 has the convergence function in the horizontal direction and divergence function in the vertical direction, while the four-poles divergence electromagnet 144 has the divergence function in the horizontal direction and has the convergence function in the vertical direction. In the horizontal divergence magnetic field which is excited by the four-poles divergence electromagnets 144, as the horizontal displacement from the center orbit of the charged particle beam is larger, the divergence force towards the outer side in the horizontal direction becomes larger. This is just the same as phenomenon that the light which has been made incident while being deviated from the center of a concave lens is deflected more outward. Therefore, the charged particle beam which is passing through the inner side in the horizontal direction of the center orbit is deflected more towards the inner side by the four-poles divergence electromagnets 144, while the charged particle beam which is passing through the outer side in the horizontal direction of the center orbit is deflected more towards the outer side by the four-poles divergence electromagnets 144.

A controller 130 controls power sources 166 and 131 which are respectively connected to the four-poles convergence electromagnet 145, the four-poles divergence electromagnet 144, the multipolar electromagnet 11 for resonance excitation, the high frequency applying unit 120, the electrostatic deflector 101, the deflecting electromagnet 102 for beam ejection and the deflecting electromagnet 146 in order to operate the accelerator 100.

The description will hereinbelow be given with respect to a method of operating the accelerator 100.

At the time when the charged particle beam has been made incident from the proceeding accelerator 98 to the accelerator 100 of interest, the controller 130 controls the associated power sources 131 in such a way that the energy is given from a high frequency acceleration cavity 148 to the charged particle beam. The controller 130 controls, while giving the energy to the charged particle beam, the associated power sources 131 so as to increase the magnetic field strength of the deflecting electromagnet 146, the four-poles convergence electromagnets 145, and the four-poles divergence electromagnets 144 to accelerate the charged particle beam up to the needed energy.

At the time when the charged particle beam has been accelerated up to the needed energy, the controller 130 controls the associated power sources 131 to excite the four-poles convergence electromagnets 145 and the four-poles divergence electromagnets 144 so that the betatron oscillation frequency of the charged particle beam is set to a predetermined suitable value. Concurrently therewith, the controller 130 controls the associated power sources 131 in order to excite the multipolar electromagnet 11 for resonance excitation so that the stability limit of the resonance is set to a predetermined value.

Next, the controller 130 controls the high frequency power source 166 for beam ejection to generate the high frequency electromagnetic field in the high frequency applying unit 120, and at the same time, controls the associated power source 131 to generate the horizontal electrostatic field between the partition electrode 1031 and the electrode 1032 of the electrostatic deflector 101 and also to generate the vertical magnetic field between the partition coil 1041 and the coil 1042 of the deflecting electromagnet 102 for beam ejection. Then, the controller 130 maintains the currents substantially fixed which are respectively supplied to the four-poles convergence electromagnets 145, the four-poles divergence electromagnets 144 and the multipolar electromagnet 11 for resonance excitation, and also maintains the stability limit fixed in which the resonance is generated.

When the high frequency electromagnetic field is applied from the high frequency applying unit 120 to the charged particle beam, the amplitude by the betatron oscillations of the charged particle beam is increased gradually so that the charged particle beam exceeds the stability limit of the resonance. Then, the charged particle beam which has exceeded the stability limit of the resonance abruptly increases the amplitude of the betatron oscillations. After the amplitude of the betatron oscillations has been abruptly increased, the charged particle beam which enters into the space defined between the electrode 1031 and the electrode 1032 of the electrostatic deflector 101 is deflected towards the outer side in the horizontal direction of the center orbit of the accelerator 100 by the electric field between the electrode 1031 and the electrode 1032.

The charged particle beam which has been deflected by the electrostatic deflector 101 is further deflected more towards the outer side in the horizontal direction by the downstream four-poles divergence electromagnet 144. Then, the charged particle beam which has been deflected towards the outer side in the horizontal direction by the four-poles divergence electromagnet 144 is further deflected more towards the outer side in the horizontal direction when passing through the next deflecting electromagnet 146. Then, the charged particle beam which has passed through the deflecting more electromagnet 146 is further deflected towards the outer side in the horizontal direction by the downstream four-poles divergence electromagnet 144. Then, the charged particle beam which has been deflected by the downstream four-poles divergence electromagnet 144 passes through the space defined between the partition coil 1041 and the coil 1042 without colliding with the partition coil 1041 and then is deflected in the direction of the transport system by the deflecting electromagnet 102 for beam ejection.

In addition, since the stability limit of the resonance is maintained substantially fixed during the ejection, the orbit of the beam which enters into the space between the electrode 1031 and the electrode 1032 is not changed at all and hence it is possible to obtain the ejected beam having the fixed ejection angle. As a result, collision of the ejected beam with the partition coil 1041 or the beam duct can be prevented reducing beam loss.

The charged particles which did not enter into the space between the partition electrode 1031 and the electrode 1032 of the electrostatic deflector 101 are not substantially deflected in the four-poles divergence electromagnets 144 and the deflecting electromagnet 146 since the horizontal displacement from the center orbit is small, and hence do not reach the partition coil 1041 in the deflecting electromagnet 102 for beam ejection. Then, such charged particle beam circulates again through the accelerator 100 and the high frequency electromagnetic field is applied thereto from the high frequency applying unit 120.

Therefore, since collision of the ejected beam collides with the coil 1041 or the beam duct, can be prevented so as to reduce beam loss, the ejection efficiency can be enhanced. For example, in the case where the electrostatic deflector 101 is 80 kV/cm in electric field strength and is 1 m in length, and the deflecting electromagnet 102 for beam ejection is 1 T in magnetic field strength and is 1 m in length, and also the partition coil 1041 having the sufficient thermal margin is employed, while if both the electrostatic deflector 101 and the deflecting electromagnet 102 for beam ejection are arranged in series in the straight section to be used as in the prior art, then the beam loss is equal to or larger than 50%, whereas in the present embodiment, the beam loss is equal to or smaller than 10%.

In addition, since the charged particle beam is sufficiently deflected through the deflecting electromagnet 146 and the four-poles divergence electromagnet 144, the electrostatic deflector 101 and the deflecting electromagnet 102 for beam ejection can be employed which have a shorter structure in the charged particle beam circulating direction as compared with the prior art. In addition, the coil 1041 of the deflecting electromagnet 102 for beam ejection can be thickened, and hence its allowable current value against heating can be increased. Further, since the electrostatic deflector 101 and the deflecting electromagnet 102 for beam ejection are not arranged between the deflecting electromagnet 146 and another deflecting electromagnet adjacent thereto, i.e., the electrostatic deflector 101 and the deflecting electromagnet 102 for beam ejection are not arranged in series in the same straight section, and the accelerator 100 can be miniaturized.

In addition, since the charged particle beam is sufficiently deflected through the deflecting electromagnet 146 and the four-poles divergence electromagnets 144, the electrostatic deflector 101 which generates the small electric field strength can be used. In addition, since the value of the current which is supplied to the deflecting electromagnet 102 for beam ejection may be small, it is possible to suppress the calorification in the partition coil 1041.

Figure 2:
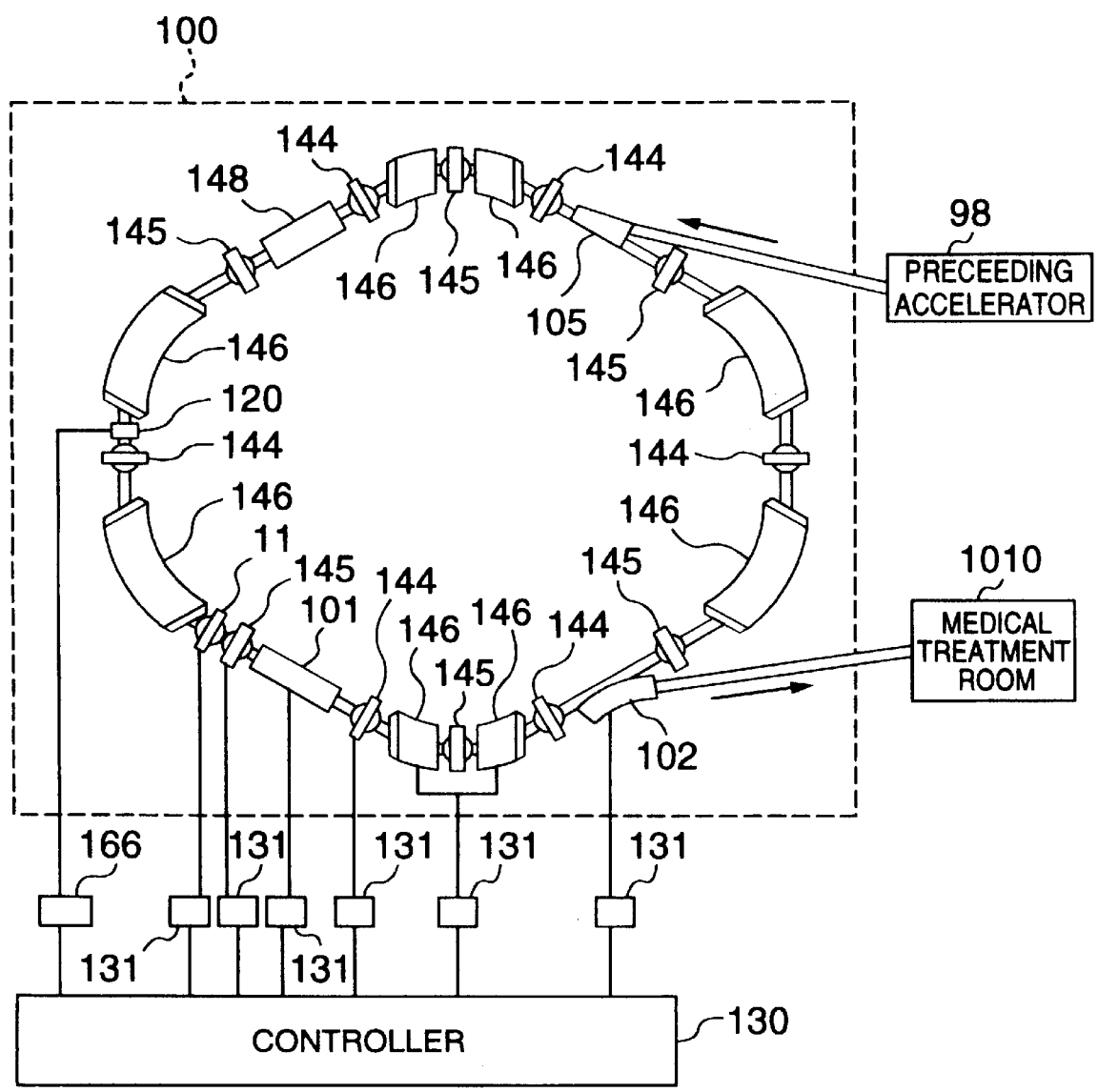
FIG. 2 is a schematic view, partly in block diagram, showing a layout of a synchrotron type accelerator as another embodiment of the present invention.

In addition, the structure may be adopted such that the deflecting electromagnet 146 shown in FIG. 1 is divided into two deflecting electromagnet portions 146 as shown in FIG. 2, and also the four-poles convergence electromagnet 145 is arranged therebetween. While in addition to the four-poles divergence electromagnets 144, the four-poles convergence electromagnet 145 is provided between the electrostatic deflector 101 and the deflecting electromagnet 102 for beam ejection, it is better that the number of four-poles divergence electromagnets 144 is larger than the number of four-poles convergence electromagnets 145.

Figure 3:
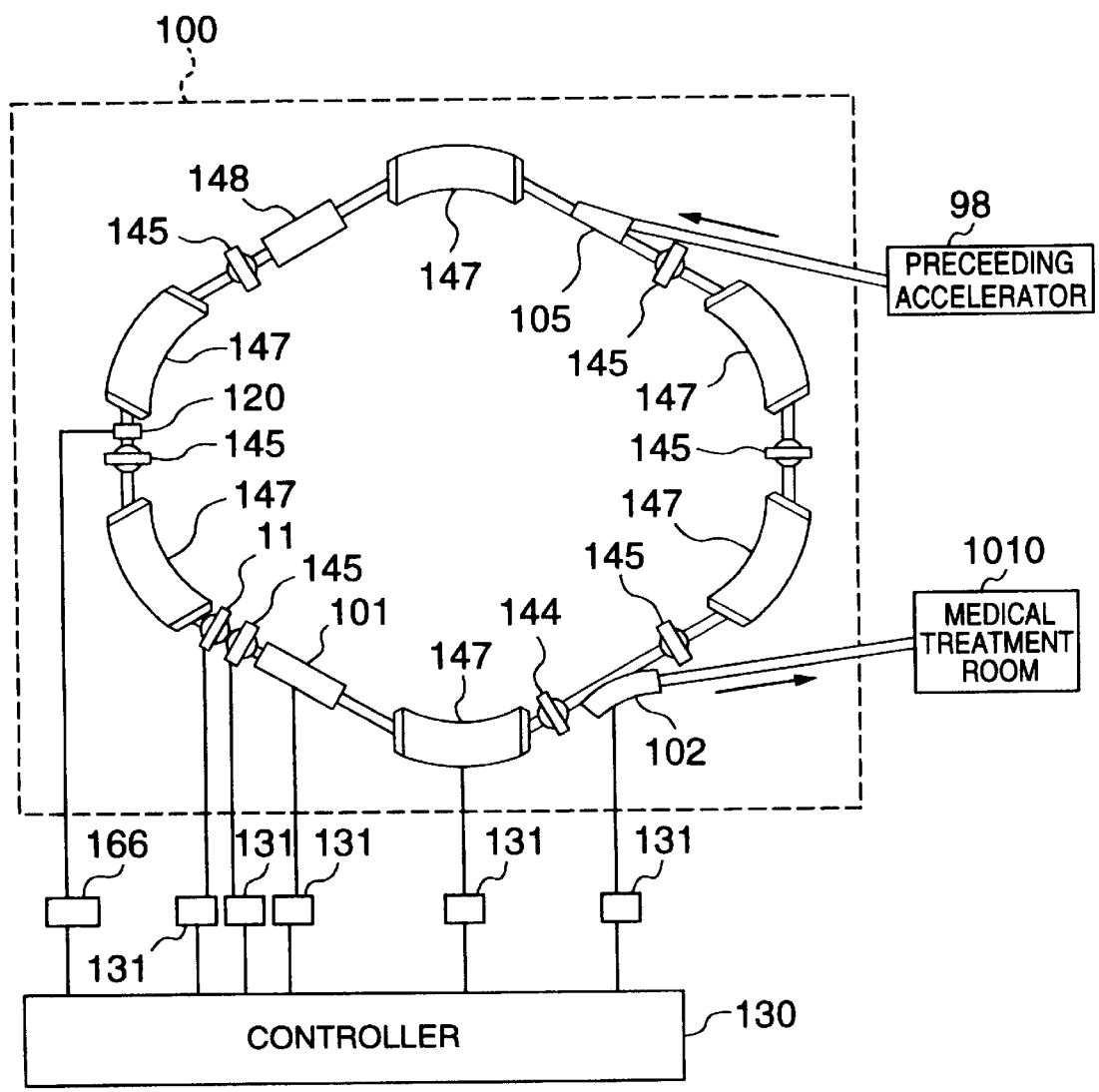
FIG. 3 schematic view, partly in block diagram, showing a layout of a synchrotron type accelerator as still another embodiment of the present invention.

Next, a synchrotron type accelerator as another embodiments of the present invention is shown in FIG. 3.

In the present embodiment, there are employed deflecting electromagnets 147 each having the divergence function in the horizontal direction and the high frequency acceleration cavity 148.

Figure 4:
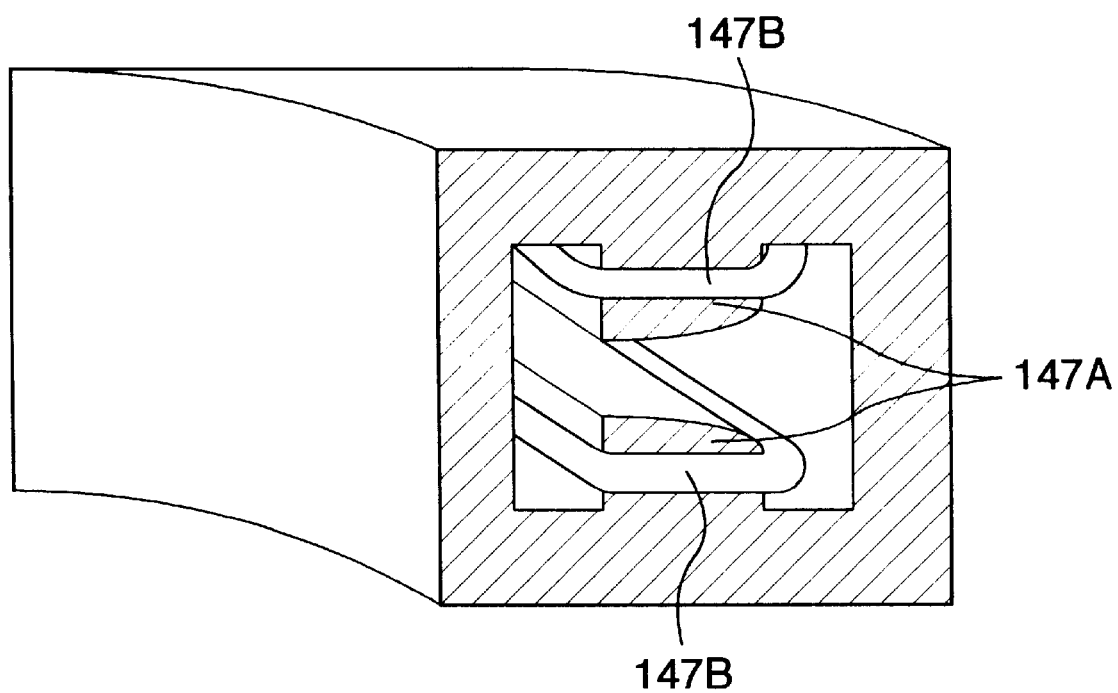
FIG. 4 is schematic view showing a structure of a deflecting e electromagnet 147 shown in FIG. 3.
Figure 5:
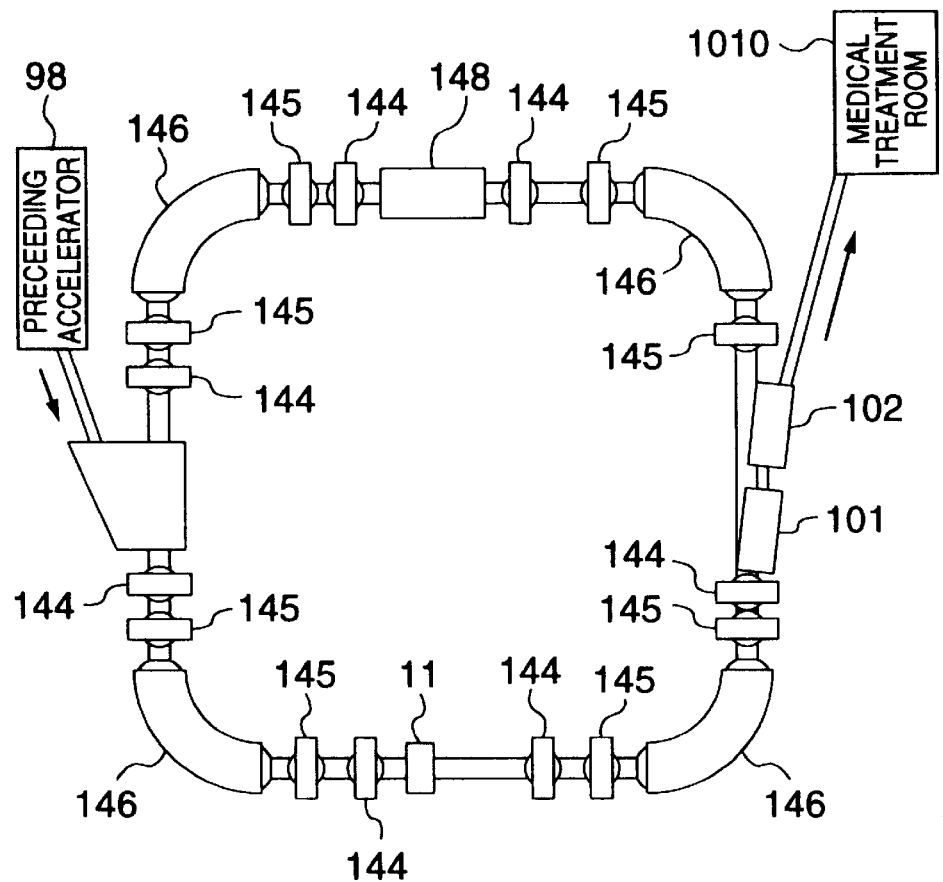
FIG. 5 is schematic view showing a layout of a conventional synchorotron type accelerator.
Figure 6:
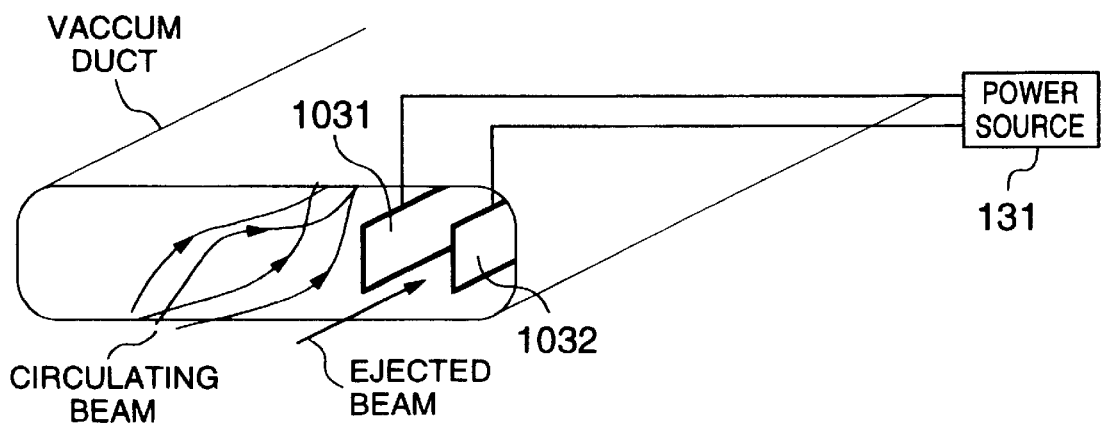
FIG. 6 is a perspective view showing a structure of an electrostatic deflector 101 for beam ejection.
Figure 7:
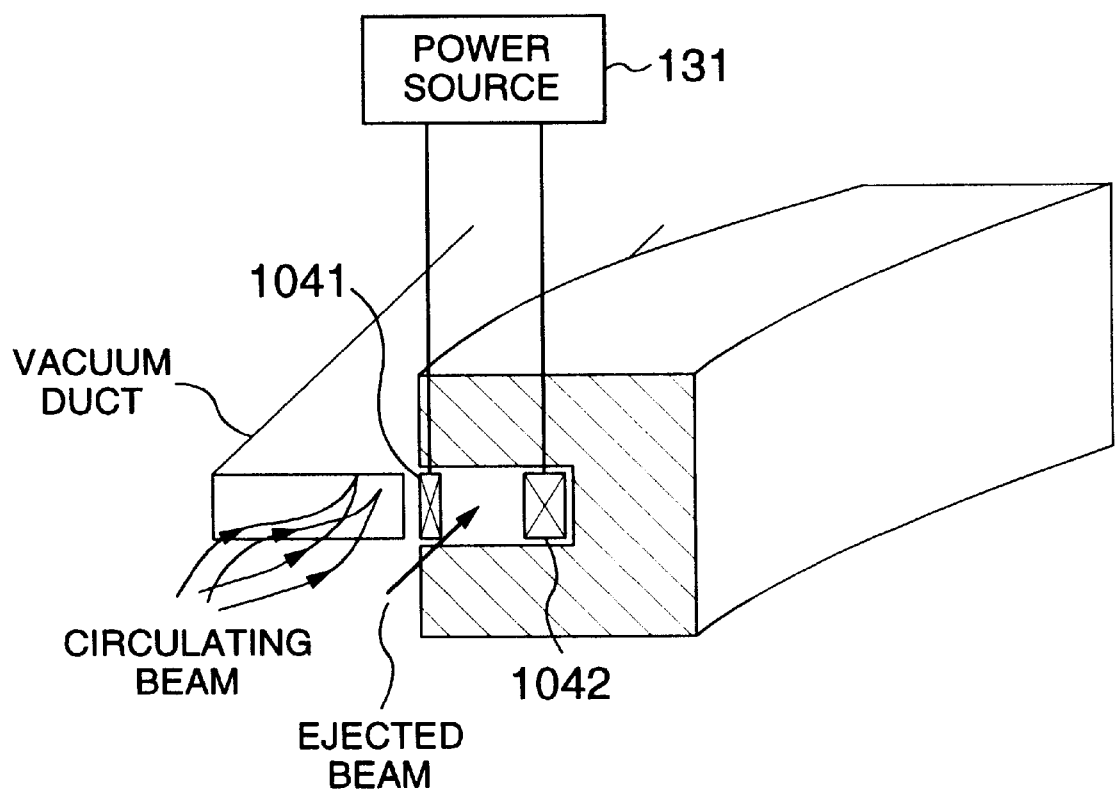
FIG. 7 is perspective view showing a structure of a deflecty electromagnet 102 for beam ejection.

The deflecting electromagnet 147 has, as shown in FIG. 4, the structure in which the spacing between magnetic poles 147A increases radially, outwardly, so that at the time when the current is supplied from the power source 131 to coils 147B, the charged particle beam is deflected and also diverges horizontally.

The charged particle beam which has been deflected towards the outer side in the horizontal direction through the electrostatic deflector 101 is further deflected more towards the outer side by the deflecting electromagnet 147 to be ejected through the downstream deflecting electromagnet 102 for beam ejection to the beam transporting system for beam ejection.

According to the present embodiment, since the number of four-poles divergence electromagnets can be reduced as compared with the first embodiment, the accelerator 100 can be further miniaturized as compared with the first embodiment.

Since if the synchrotron type accelerator of the first or second embodiment is applied to a medical treatment irradiation system, then the ejected beam can be obtained with high ejection efficiency, the irradiation quantity of charged particle beam required for a patient can be achieved for a short irradiation time. Therefore, the irradiation time can be decreased, and also one medical treatment time per patient can also be reduced.

While the invention has been particularly shown and described with reference to the preferred embodiments, it will be understood by those skilled in the art that various modifications may be made therein without departing from the spirit and scope of the invention.

What is claimed is:

1. A synchrotron type accelerator including: at least one deflecting electromagnet arranged on a circulating orbit of a charged particle beam; four-poles divergence electromagnets and four-poles convergence electromagnets arranged on said circulating orbit; a high frequency applying unit arranged on said circulating orbit for applying a high frequency electromagnetic field to said charged particle beam which circulates and for increasing an amplitude of betatron oscillation of said charged particle beam to a level above a stability limit of resonance; a first deflector for beam ejection arranged on said circulating orbit for deflecting said charged particle beam which is excited above said stability limit of the resonance by said high frequency applying unit; and a second deflector for beam ejection arranged on said circulating orbit used in pair with said first deflector for beam ejection for introducing said charged particle beam deflected by said first deflector for beam ejection into an ejected beam transporting system;

wherein said at least one deflecting electromagnet and said second deflector for beam ejection are arranged in this order downstream with respect to said first deflector for beam ejection, and said at least one deflecting electromagnet deflects said charged particle beam deflected by said first deflector for beam ejection toward said second deflector for beam ejection.

2. A synchrotron type accelerator according to claim 1, further comprising:

a power source for supplying power to generate an electric field or a magnetic field in said at least one deflecting electromagnet, said four-poles divergence electromagnets, said four-poles convergence electromagnets, said first deflector for beam ejection and said second deflector for beam ejection; and control means for controlling said power source so that the strength of said electric field or said magnetic field is maintained at a substantially constant level, while said high frequency applying unit is applying said high frequency electromagnetic field to said charged particle beam.

3. A medical treatment system comprising:

a synchrotron type accelerator according to claim 1;

said ejected beam transporting system for transporting a charged particle beam ejected from said synchrotron type accelerator; and an irradiation system connected to said ejected beam transporting system for irradiating said charged particle beam transported by said ejected beam transporting system to a patient.

4. A synchrotron type accelerator including: at least one deflecting electromagnet arranged on a circulating orbit of a charged particle beam; four-poles divergence electromagnets and four-poles convergence electromagnets arranged on said circulating orbit; a high frequency applying unit arranged on said circulating orbit for applying a high frequency electromagnetic field to said charged particle beam which circulates and for increasing an amplitude of betatron oscillation of said charged particle beam to a level above a stability limit of resonance; a first deflector for beam ejection arranged on said circulating orbit for deflecting said charged particle beam excited above said stability limit of the resonance by said high frequency applying unit; and a second deflector for beam ejection arranged on said circulating orbit used in pair with said first deflector for beam ejection for introducing said charged particle beam deflected by said first deflector into an ejected beam transporting system;

wherein said at least one deflecting electromagnet and said second deflector for beam ejection are arranged in this order downstream with respect to said first deflector for beam ejection, and at least one of said four-poles divergence electromagnets is located downstream with respect to said first deflector for beam ejection and upstream with respect to said second deflector for beam ejection.

5. A synchrotron type accelerator according to claim 4, wherein two of said four-poles divergence electromagnets are located downstream with respect to said first deflector for beam ejection and upstream with respect to said second deflector for beam ejection.

6. A synchrotron type accelerator according to claim 4, further comprising:

a power source for supplying power to generate an electric field or a magnetic field in said at least one deflecting electromagnet, said four-poles divergence electromagnets, said four-poles convergence electromagnets, said first deflector for beam ejection and said second deflector for beam ejection; and control means for controlling said power source so that the strength of said electric field or said magnetic field is maintained at a substantially constant level, while said high frequency applying unit is applying said high frequency electromagnetic field to said charged particle beam.

7. A medical treatment system comprising:

a synchrotron type accelerator according to claim 4;

said ejected beam transporting system for transporting a charged particle beam ejected from said synchrotron type accelerator; and an irradiation system connected to said ejected beam transporting system for irradiating said charged particle beam transported by said ejected beam transporting system to a patient.

* * * * *